US007528119B2

(12) United States Patent
Yerxa et al.

(10) Patent No.: US 7,528,119 B2
(45) Date of Patent: *May 5, 2009

(54) DI(URIDINE 5'-)TETRAPHOSPHATE AND SALTS THEREOF

(75) Inventors: Benjamin R. Yerxa, Raleigh, NC (US); Edward G. Brown, Cary, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 227 days.

This patent is subject to a terminal disclaimer.

(21) Appl. No.: 11/486,497

(22) Filed: Jul. 14, 2006

(65) Prior Publication Data

US 2006/0258615 A1    Nov. 16, 2006

Related U.S. Application Data

(60) Division of application No. 11/055,170, filed on Feb. 9, 2005, now Pat. No. 7,132,410, which is a continuation of application No. 10/413,965, filed on Apr. 14, 2003, now Pat. No. 6,872,710, which is a continuation-in-part of application No. 09/990,546, filed on Nov. 20, 2001, now Pat. No. 6,548,658, which is a continuation-in-part of application No. 09/122,516, filed on Jul. 24, 1998, now Pat. No. 6,319,908.

(60) Provisional application No. 60/054,147, filed on Jul. 25, 1997.

(51) Int. Cl.
*A61K 31/70* (2006.01)
(52) U.S. Cl. ........................................................ 514/51
(58) Field of Classification Search .................. 514/51
See application file for complete search history.

(56) References Cited

U.S. PATENT DOCUMENTS

| 4,136,175 A | 1/1979 | Rideout et al. ............... 424/180 |
| 5,032,680 A | 7/1991 | Kawai et al. ................... 536/23 |
| 5,449,664 A | 9/1995 | Verheyden et al. ............. 514/45 |
| 5,635,160 A | 6/1997 | Stutts, III et al. .............. 424/45 |
| 5,763,447 A | 6/1998 | Jacobus et al. ............... 514/265 |
| 5,789,391 A | 8/1998 | Jacobus et al. ................ 514/51 |
| 5,837,861 A | 11/1998 | Pendergast et al. .......... 536/25.6 |
| 5,900,407 A | 5/1999 | Yerxa et al. .................... 514/47 |
| 6,258,374 B1 | 7/2001 | Friess et al. .................. 424/436 |
| 6,319,908 B1 | 11/2001 | Yerxa et al. .................... 514/51 |
| 6,348,589 B1 | 2/2002 | Pendergast et al. .......... 536/25.6 |
| 6,548,658 B2 | 4/2003 | Yerxa ........................ 536/26.22 |
| 6,555,675 B2 | 4/2003 | Rideout et al. .............. 536/25.6 |
| 6,596,725 B2 | 7/2003 | Peterson et al. .............. 514/256 |
| 6,696,425 B2 | 2/2004 | Yerxa et al. .................... 514/47 |
| 6,818,629 B2 | 11/2004 | Peterson et al. ................ 514/47 |
| 6,838,449 B2 | 1/2005 | Agsharian .................... 514/54 |
| 6,867,199 B2 | 3/2005 | Rideout et al. ................ 514/47 |
| 6,872,710 B2 | 3/2005 | Yerxa et al. .................... 514/47 |
| 6,887,858 B1 | 5/2005 | Yerxa et al. .................... 514/47 |
| 6,916,794 B2 | 7/2005 | Yerxa et al. .................... 514/47 |
| 6,921,755 B2 | 7/2005 | Yerxa et al. .................... 514/47 |
| 6,977,246 B2 | 12/2005 | Pendergast et al. ............ 514/47 |
| 7,078,391 B2 | 7/2006 | Peterson et al. ................ 514/47 |

FOREIGN PATENT DOCUMENTS

| JP | 07-242685 A | 9/1995 |
| WO | WO98/34593 | 8/1998 |
| WO | WO98/34942 | 8/1998 |
| WO | WO99/05155 | 2/1999 |
| WO | WO99/61012 | 12/1999 |
| WO | WO00/20430 | 4/2000 |
| WO | WO00/39145 | 7/2000 |
| WO | WO01/02416 | 1/2001 |
| WO | WO02/060454 | 8/2002 |

OTHER PUBLICATIONS

Coste et al., "Non-adenylated Bis(5'-nucleosidyl) Tetraphosphates Occur in *Saccaromyces cerevisiae* and in *Esherichia coli* and Accumulate upon Temperature Shift or Exposure to Cadmium," *Journal of Biological Chemistry*, 262(25), 12096-12103 (Sep. 5, 1987).

Ng, E. and Orgel, L., "The action of a water-soluble carbodiimide and adenosine-5'-polyphosphates," *Nucleic Acid Res.*, 15(8): 3573-3580 (1987).

Rapaport et al., "HeLa cell DNA polymerase $\alpha$ is tightly associate with tryptophanyl-tRNA synthetase and diadenosine 5',5'''-$P^1,P^4$-tetraphosphate binding activities," Proc. Natl. Acad. Sci., 78(2): 838-842 (1981).

Sillero et al., "Dinucleosidetriphosphatase from Ral Liver—Purification and Properties," *European Journal of Biochemistry*, 76(2), 331-337 (Jun. 15, 1977).

Vallejo et al., "Dinucleosidetriphosphatase in Rat Liver and *Artemia Salina*," *Biochimica et Biophysica Acta*, 438, 304-309 (1976).

*Primary Examiner*—Elli Peselev
(74) *Attorney, Agent, or Firm*—Howery LLP; Viola T. Kung

(57) ABSTRACT

The present invention are directed to $P^1,P^4$-di(uridine 5'-)tetraphosphate, tetra-alkali metal salts such as tetrasodium, tetralithium, tetrapotassium, and mixed tetra-alkali metal cations thereof. The tetra alkali metal salts of $P^1,P^4$-di(uridine 5'-)tetraphosphate are water-soluble, nontoxic, and easy to handle during manufacture. These tetra-monovalent alkali metal salts are more resistant to hydrolysis than the mono-, di-, or tri-acid salts, therefore, they provide an improved stability and a longer shelf life for storage. The present invention also provides methods for the synthesis of $P^1,P^4$-di(uridine 5'-)tetraphosphate, and its pharmaceutically acceptably acceptable salts thereof, and demonstrates the applicability to the production of large quantities. The methods substantially reduce the time required to synthesize diuridine tetraphosphate, for example, to three days or less.

6 Claims, No Drawings

DI(URIDINE 5'-)TETRAPHOSPHATE AND SALTS THEREOF

This application is a divisional application of U.S. application Ser. No. 11/055,170, filed Feb. 9, 2005, U.S. Pat. No. 7,132,410; which is a continuation of U.S. application Ser. No. 10/413,965, filed Apr. 14, 2003, U.S. Pat. No. 6,872,710; which is a continuation-in-part of U.S. application Ser. No. 09/990,546, filed Nov. 20, 2001, U.S. Pat. No. 6,548,658, which is a continuation-in-part of U.S. application Ser. No. 09/122,516, filed Jul. 24, 1998, U.S. Pat. No. 6,319,908, which claims the benefit of U.S. Provisional Application No. 60/054,147 filed Jul. 25, 1997. The above applications are incorporated herein by reference in their entirety.

TECHNICAL FIELD

This invention relates to novel therapeutic dinucleotide salt compositions and methods for production such. More specifically, it relates to $P^1,P^4$-di(uridine 5'-)tetraphosphate ($U_2P_4$), tetrasalt and the pharmaceutical formulation thereof.

BACKGROUND OF THE INVENTION $P^1,P^4$-Di(uridine 5'-)tetraphosphate is a dinucleotide of the following structure:

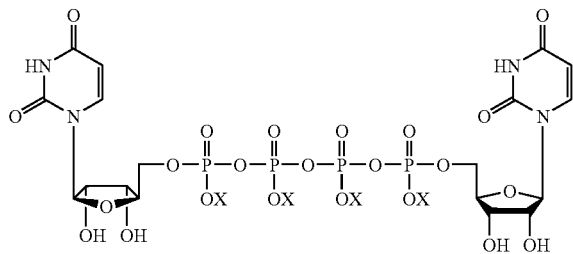

The free acid of $P^1,P^4$-di(uridine 5'-)tetraphosphate, where X is hydrogen, has been previously described as uridine 5'-(pentahydrogen tetraphosphate), $P'''\rightarrow 5'$-ester with uridine (CAS Registry Number: 59985-21-6; C. Vallejo et al., *Biochimica et Biophysica Acta* 438, 305 (1976) and H. Coste et al., *J. Biol. Chem.* 262, 12096 (1987)).

Different methods have been described for the synthesis of purine dinucleotides such as diadenosine tetraphosphate ($A_2P_4$) (E. Rappaport et al, *Proc. Natl. Acad. Sci*, 78, 838, (1981); A. Guranowski et al, *Biochemistry*, 27, 2959, (1988); C. Lobaton et al, *Eur. J. Biochem.*, 50, 495, 1975; K. Ng and L. Orgel, *Nucl. Acid Res.*, 15, 3573, (1987)). However, this has not been true for $U_2P_4$ which is a pyrimidine nucleotide. Although purine nucleotides and pyrimidine nucleotides appear to be analogous, the methods used for purine nucleotide synthesis do not necessarily work for pyrimidines such as uridine.

Several references describe protocols for the production of diuridine tetraphosphate. The methods described in the literature are very time consuming, lasting over five days and producing only small amounts of diuridine tetraphosphate (C. Vallejo et al., *Biochimica et Biophysica Acta* 438, 305 (1976), Sillero et al., *Eur J Biochem* 76, 332 (1972)). According to this technique, diuridine tetraphosphate was synthesized through a reaction of uridine 5'-monophosphomorpholidate with the triethylamine salt of pyrophosphoric acid in a medium of anhydrous pyridine. After 5 days at 30° C., pyridine was removed from the reaction mixture by evaporation, and the residue resuspended in glass-distilled water, the suspension applied to a DEAE-cellulose column and fractionated with a linear gradient (0.06-0.25 M) of ammonium bicarbonate, pH 8.6. The peak eluting between 0.17-0.19 M ammonium bicarbonate was partially characterized as $U_2P_4$ by the following criteria: insensitivity to alkaline phosphatase, phosphorus to base ratio and analysis of the products of hydrolysis (UTP+UMP), after treatment with phosphodiesterase I, by electrophoresis in citrate buffer, pH 5.0. No yield or spectroscopic data were given. Thus, these procedures for the synthesis of diuridine tetraphosphate are lengthy and produce only small amounts of only partially characterized diuridine tetraphosphate.

Diuridine tetraphosphate has been shown to have beneficial properties in the treatment of various diseases, such as chronic obstructive pulmonary disease (COPD). For example, it has been demonstrated to facilitate the clearance of mucous secretions from the lungs of a subject such as a mammal including humans in need of treatment for various reasons, including cystic fibrosis, chronic bronchitis, asthma, bronchiectasis, post-operative mucous retention, pneumonia, primary ciliary dyskinesia (M. J. Stutts, III, et al, U.S. Pat. No. 5,635,160; PCT International Publication WO 96/40059) and the prevention and treatment of pneumonia in immobilized patients (K. M. Jacobus and H. J. Leighton, U.S. Pat. No. 5,763,447). Further therapeutic uses include treatment of sinusitis (U.S. Pat. Nos. 5,789,391; 5,972,904; 5,981,506; 5,958,897; and PCT International Publication WO 98/03177), otitis media (U.S. Pat. No. 6,423,694; PCT International Publication WO 97/29756), dry eye (U.S. Pat. No. 5,900,407; PCT International Publication WO 98/34593), retinal detachment (PCT International Publication WO 02/060454), nasolacrimal duct obstruction (Publication No. US-2002-0103157-A1), the treatment of female infertility and irritation due to vaginal dryness via increased mucus secretions and hydration of the epithelial surface (U.S. Pat. No. 6,462,028; PCT International Publication WO 00/30629), and enhancing the performance of athletes.

SUMMARY OF THE INVENTION

The present invention are directed to $P^1,P^4$-di(uridine 5'-)tetraphosphate, tetra-alkali metal salts such as tetrasodium, tetralithium, tetrapotassium, and mixed tetra-alkali metal cations thereof. The tetra alkali metal salts of $P^1,P^4$-di(uridine 5'-)tetraphosphate are water-soluble, nontoxic, and easy to handle during manufacture. These tetra-monovalent alkali metal salts are more resistant to hydrolysis than the mono-, di-, or tri-acid salts, therefore, they provide an improved stability and a longer shelf life for storage. The present invention also provides methods for the synthesis of $P^1,P^4$-di(uridine 5'-)tetraphosphate, and its pharmaceutically acceptably salts thereof, and demonstrates the applicability to the production of large quantities. The methods of the present invention substantially reduce the time required to synthesize diuridine tetraphosphate, for example, to three days or less.

Another aspect of the present invention is a pharmaceutical formulation comprising $P^1,P^4$-di(uridine 5')-tetraphosphate, tetra-alkali metal salt, in a pharmaceutically acceptable carrier, in the form of an aqueous, a gel, a gel-like, or a solid formulation.

Another aspect of the present invention are methods of treating various disease states, including, but not limited to: chronic obstructive pulmonary diseases, sinusitis, otitis media, nasolacrimal duct obstruction, dry eye disease, retinal detachment, pneumonia, and female infertility or irritation caused by vaginal dryness.

DETAILED DESCRIPTION OF THE INVENTION

The present invention provides methods for the synthesis of the therapeutic dinucleotide, $P^1,P^4$-di(uridine 5'-)tetraphosphate, and the salts thereof, which demonstrate large quantity production. The methods of the present invention substantially reduce the time period required to synthesize $P^1,P^4$-di(uridine 5'-)tetraphosphate, for example, to three days or less.

The present invention also provides novel tetra-monovalent alkali metal salts of $P^1, P^4$-di(uridine 5'-)tetraphosphate, irrespective of the method of making them. The tetra alkali metal salts of $P^1,P^4$-di(uridine 5'-)tetraphosphate (Formula I) are stable, soluble, nontoxic, and easy to handle during manufacture.

Formula I

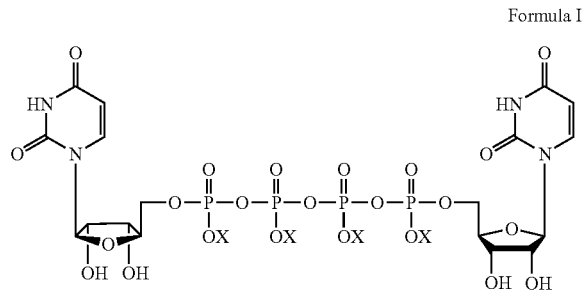

wherein:
each X is independently Li, Na, or K.

Formula I include tetra-monovalent alkali metal salts of $P^1,P^4$-di(uridine 5'-) tetraphosphate, such as tetrasodium, tetralithium, and tetrapotassium salts and tetra-mixed alkali metal salts. The tetra-mixed alkali metal cations of the tetra-mixed alkali metal salts preferably are monosodium/tripotassium, disodium/dipotassium, trisodium/monopotassium, monopotassium/trilithium, dipotassium/dilithium, tripotassium/monolithium, monosodium/trilithium, disodium/dilithium, trisodium/monolithium, and monosodium/monolithium/dipotassium, monosodium/dilithium/monopotassium and disodium/monolithium/monopotassium cations.

The tetra-alkali metal salts of $P^1,P^4$-di(uridine 5'-)tetraphosphate have many advantages, for example, they provide good long-term stability profiles compared with those of divalent cations (e.g. $Ca^{2+}$, $Mg^{2+}$, $Mn^{2+}$), which catalyze the hydrolysis of phosphate esters. Furthermore, unlike ammonium salts, they cannot release ammonia during long-term storage, and hence are more stable.

These inorganic sodium, lithium, and potassium cations impart excellent water solubility compared with hydrophobic amine salts such as tri- and tetrabutylammonium, and similar salts. High water solubility is an important advantage for flexibility in pharmaceutical formulations of varying concentration.

The tetra-alkali metal salts of $P^1,P^4$-di(uridine 5'-)tetraphosphate are non-irritating to the lung and eyes. Other cations may be irritating to the lungs, eyes, and other mucosal epithelia, or are otherwise not well tolerated by the human body.

These tetra-alkali metal salts of $P^1,P^4$-di(uridine 5'-)tetraphosphate have a high degree (>90%) of purity, thus are suitable for pharmaceutical use. Furthermore, these tetra-alkali metal salts are more resistant to hydrolysis than the mono-, di-, or tri-acid salts, therefore, they provide an improved stability and a longer shelf life for storage. In addition, these salts are easily handled as white solids, compared to an oil or gum as with some amine salts.

The present invention provides a pharmaceutical formulation comprising the compound of Formula I, in a pharmaceutically acceptable carrier, in the form of an aqueous, a gel, a gel-like, or a solid formulation. In one embodiment of the invention, the pharmaceutical formulation is in the form of an aqueous solution and comprises physiologically safe excipients formulated to osmolarity between 250-350 mOsm and pH 5-9. A preferred osmolarity is between about 280 and 320 mOsm, or 280 and 300 mOsm. A preferred pH is between about 6.8 and 7.8, or about 7.0 and 7.6. In one embodiment of the invention, the pharmaceutical formulation is sterile.

The pharmaceutical formulation comprising tetra-alkali metal salts of $P^1,P^4$-di(uridine 5'-)tetraphosphate (Formula I) can be used to facilitate the clearance of mucous secretions from the lungs of a subject such as a mammal including humans in need of treatment for various reasons, including cystic fibrosis, chronic bronchitis, asthma, bronchiectasis, post-operative mucous retention, pneumonia, primary ciliary dyskinesia (M. J. Stutts, III, et al, U.S. Pat. No. 5,635,160; PCT International Publication WO 96/40059) and the prevention and treatment of pneumonia in immobilized patients (K. M. Jacobus and H. J. Leighton, U.S. Pat. No. 5,763,447). Further therapeutic uses include treatment of sinusitis (U.S. Pat. Nos. 5,789,391; 5,972,904; 5,981,506; 5,958,897; and PCT International Publication WO 98/03177), otitis media (U.S. Pat. No. 6,423,694; PCT International Publication WO 97/29756), dry eye (U.S. Pat. No. 5,900,407; PCT International Publication WO 98/34593), retinal detachment (PCT International Publication WO 02/060454), nasolacrimal duct obstruction (Publication No. US-2002-0103157-A1), the treatment of female infertility and irritation due to vaginal dryness via increased mucus secretions and hydration of the epithelial surface (U.S. Pat. No. 6,462,028; PCT International Publication WO 00/30629), and enhancing the performance of athletes.

The compounds of Formula I can be administered orally, topically, parenterally, by inhalation or spray, intra-operatively, rectally, or vaginally in dosage unit formulations containing conventional non-toxic pharmaceutically acceptable carriers, adjuvants and vehicles. The term topically as used herein includes patches, gels, creams, ointments, suppositories, pessaries, or nose, ear or eye drops. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers or diluents or adjuvants and, if desired, other active ingredients. One such carrier would be sugars, where the compounds may be intimately incorporated in the matrix through glassification or simply admixed with the carrier (e.g., lactose, sucrose, trehalose, mannitol) or other acceptable excipients for lung or airway delivery.

One or more compounds of general Formula I may be administered separately or together, or separately or together with: mucolytics such as DNAse (Pulmozyme®) or acetylcysteine, antibiotics, including but not limited to inhaled Tobramycin®; non-steroidal anti-inflammatories, antivirals, vaccines, decongestants and corticosteroids.

The pharmaceutical compositions containing compounds of general Formula I may be in a form suitable for oral use, for example, as tablets, caplets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example, peanut oil, liquid paraffin or olive oil.

Aqueous suspensions contain the active materials in admixture with excipients suitable for the manufacture of aqueous suspensions. Such excipients are suspending agents, for example: sodium carboxymethylcellulose, methylcellulose and sodium alginate. Dispersing or wetting agents may be a naturally-occurring phosphatide or condensation products of an allylene oxide with fatty acids, or condensation products of ethylene oxide with long chain aliphatic alcohols, or condensation products of ethylene oxide with partial esters from fatty acids and a hexitol, or condensation products of ethylene oxide with partial esters derived from fatty acids and hexitol anhydrides. Those skilled in the art will recognize the many specific excipients and wetting agents encompassed by the general description above. The aqueous suspensions may also contain one or more preservatives, for example, ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredients in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Compounds of Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle. The sterile injectable preparation may be a sterile injectable solution or suspension in a non-toxic parentally acceptable diluent or solvent. Among the acceptable vehicles and solvents that may be employed are sterile water, saline solution, or Ringer's solution. The compounds of general Formula I may also be administered in the form of suppositories for ear, rectal or vaginal administration of the drug.

These compositions can be prepared by mixing the drug with a suitable non-irritating excipient which is solid at ordinary temperatures but liquid at the body temperature and will therefore melt to release the drug. Such materials are cocoa butter and polyethylene glycols.

Solutions of compounds of Formula I may be administered by intra-operative installation at any site in the body.

Single dosage levels of the order of from about 1 to about 400 mg, preferably in the range of 10 to 300 mg, and most preferably in the range of 25 to 250 mg, are useful in the treatment of the above-indicated respiratory conditions. Single dosage levels of the order of from about 0.0005 to about 5 mg, preferably in the range of 0.001 to 3 mg and most preferably in the range of 0.025 to 1 mg, are useful in the treatment of the above-indicated ophthalmic conditions. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The present invention provides the synthesis of diuridine tetraphosphate tetrasodium salt via the tetraammonium salt. In this process, uridine 5'-diphosphate disodium salt is first converted to the tributylammonium salt using a sulfonic acid resin to generate UDP as the free acid, followed by salt formation with excess tributylamine. After isolation by evaporative water removal, the anhydrous UDP tributylammonium salt is activated with 1,1-carbonyldiimidazole in DMF solution, during which time coupling to form $U_2P_4$ also occurs. Concentration of the solution in vacuo, followed by ion-exchange chromatography on Sephadex DEAE-A25 using an increasing gradient of aqueous ammonium bicarbonate yielded a solution of pure diuridine tetraphosphate in ammonium bicarbonate buffer. The volatile buffer is removed by repeated evaporation with water on a rotary evaporator to generate the tetraammonium salt of $U_2P_4$ as oil. The oil is dissolved in deionized water to give a ca. 10% solution, and this solution is charged to a Dowex 50W×4 $Na^+$ (Dow) column and eluted with deionized water. The fractions containing $U_2P_4$ are pooled, concentrated and lyophilized to yield $U_2P_4$ tetrasodium salt as a white solid.

Diuridine tetraphosphate tetrasodium salt has also been synthesized and crystallized by researchers at Yamasa Corporation using uridine monophosphate tributylamine salt, diphenylphosphorochloridate and triethylammonium pyrophosphate (H. Maeda, et al, WO/0020430). The crude material is purified by anion exchange chromatography and carbon chromatography to give the diuridine tetraphosphate tetrasodium salt. Crystals of this material are obtained by crystallization from a hydrophilic organic solvent and are suitable for use in x-ray crystallographic analysis of the salt. This reference is incorporated herein by reference.

The tetrammonium, tetrasodium, tetralithium and tetrapotassium salts of $P^1,P^4$-di(uridine 5'-)tetraphosphate are readily purified by aqueous ion chromatography in which no organic solvents are used.

The monosodium/tripotassium, disodium/dipotassium, trisodium/monopotassium, monopotassium/trilithium, dipotassium/dilithium, tripotassium/monolithium, monosodium/trilithium, disodium/dilithium, trisodium/monolithium, monosodium/monolithium/dipotassium, monosodium/dilithium/monopotassium and disodium/monolithium/monopotassium salts of $P^1,P^4$-di(uridine 5'-)tetraphosphate salts of $P^1,P^4$-di(uridine 5'-)tetraphosphate are advantageous in that they are readily obtained in highly purified form directly from the di(uridine 5'-)tetraphosphate tetraammonium salt.

An alternative method of making these mixed salts without the use of a cation exchange resin is to directly add alkali metal bases to an aqueous solution of the di(uridine 5'-)tetraphosphate tetraammonium salt, followed by evaporation of the resulting volatile ammonium salts under reduced pressure at about 60° C. or below. This method is an alternative method to the current method of preparing tetraammonium, tetrasodium, tetralithium and tetrapotassium salts of $P^1,P^4$-di(uridine 5'-)tetraphosphate, in that no ion exchange resin is used for the conversion of the tetraammonium salt to the mixed-alkali metal salt, and thus the new process allows for the direct preparation of mixed-alkali metal salts of di(uridine 5'-)tetraphosphate with specific ratios of alkali metals present in the composition. The step of using a cation exchange resin is not required in this new procedure.

The synthetic methods described below encompass several synthetic strategies for producing $P^1,P^4$-di(uridine 5'-)tetraphosphate. Generally, all the methods use uridine or uridine nucleotide compounds from Formula IIa-d as starting materials, which are dissolved in a polar, aprotic organic solvent (e.g. dimethylformamide, dimethylsulfoxide, dioxane, N-methylpyrrolidone, trimethylphosphate) and a hydrophobic amine (e.g. triethylamine, tributylamine, trioctylamine, 2,4,6-collidine, tetrabutylammonium, tri- and tetra-alkyl amines, heterocyclic amines). The product is obtained by phosphorylating with a phosphorylating agent from Formula IV (e.g. phosphorus oxychloride, pyrophosphate, pyrophosphorylchloride) or activating a phosphate group with an activating agent from Formula III (e.g. carbonyldiimidazole, an alky or aryl carbodiimide, an alkyl or aryl phosphochloridate), respectively, with subsequent purification various means well known to those of skill in the art, including, but not limited to, ion chromatography (e.g. DEAE Sephadex, DEAE cellulose, Dowex 50, anion and cation exchange resins). Each tetra-alkali metal salt is generated from the purified tetraammonium salt using alkali metal bases that generate ammonia or volatile salts in the presence of ammonium ions (e.g. sodium hydroxide, sodium bicarbonate, sodium acetate, potassium carbonate, potassium bicarbonate, potassium acetate, lithium formate) in a ratio which provides the desired tetra-alkali metal salt of $P^1,P^4$-di(uridine 5'-)tetraphosphate after evaporation of the volatile salts and materials present.

The method of synthesizing compounds of Formula I is carried out generally by the following steps: 1) dissolving uridine or uridine nucleotide compounds of Formulas IIa-d in a polar, aprotic organic solvent and a hydrophobic amine; 2) phosphorylating with a phosphorylating agent of one of the Formulas IVa-b to yield an amine salt of a compound of Formula IA, or activating a phosphate group of the uridine nucleotide compound with an activating agent of one of the Formulas IIa-c and reacting with a suitable compound of Formula II b-d to yield an amine salt of a compound of Formula IA; 3) purifying by ion exchange chromatography using a volatile ammonium-salt buffer such as ammonium bicarbonate, ammonium formate or ammonium acetate; and 4) evaporating the volatile aqueous buffer solution and re-evaporating with water several times to give the pure tetraammonium salt. An aqueous solution of this ammonium salt is treated with between zero and four equivalents of sodium ion, in the form of sodium hydroxide, -alkoxide, -formate, -acetate, -trifluoroacetate, -carbonate or -bicarbonate base, and between zero and four equivalents of potassium ion, in the form of potassium hydroxide, -alkoxide, -formate, -acetate, -trifluoroacetate, -carbonate or -bicarbonate base, and between zero and four equivalents of lithium ion, in the form of lithium hydroxide, -alkoxide, -formate, -acetate, -trifluoroacetate, -carbonate or -bicarbonate base, such that a total of four equivalents of alkali metals are present for each equivalent of diuridine tetraphosphate and the four equivalents of ammonium ion present in diuridine tetraphosphate tetraammonium salt. The aqueous solution of the desired mixed salt of $U_2P_4$ shown in Formula is then evaporated to dryness to remove volatile ammonium salts and solvent under vacuum. Water is added and the material is concentrated at below 60° C. on a rotary evaporator under vacuum several times to remove traces of ammonia, volatile ammonium salts and solvent. Water is added to give an approximately 10% aqueous solution, and this is lyophilized to give the desired tetra salt of diuridine tetraphosphate.

The pyrimidine β-D-ribofuranosyl starting materials uridine, uridine 5'-monophosphate (UMP), uridine 5'-diphosphate (UDP), and uridine 5'-triphosphate (UTP) are shown as free acids in Formulas IIa-d below, respectively. These materials are all commercially available in large quantity in various salt forms.

Formula IIa:

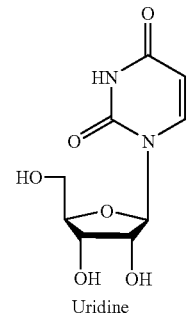

Uridine

Formula IIb:

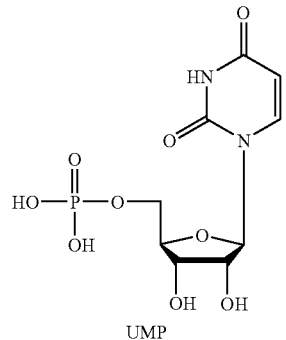

UMP and salts thereof;

Formula IIc:

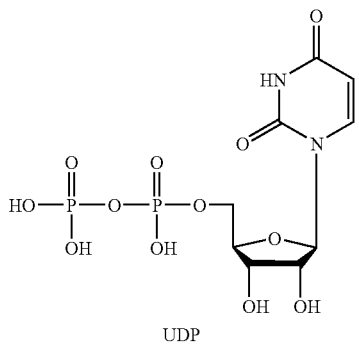

UDP and salts thereof;

Formula IId:

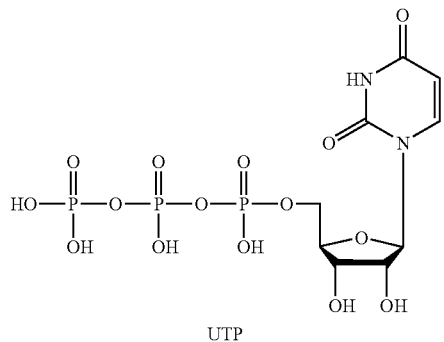

UTP and salts thereof.

The activating agents carbodiimide, activated carbonyl, and activated phosphorus compounds are shown in the general Formulas IIIa-c below, respectively.

Formula IIIa:

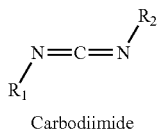

Carbodiimide wherein $R_1$ and $R_2$ are $C_1$-$C_8$ alkyl or cycloalkyl, $C_1$-$C_8$ optionally substituted alkyl or cycloalkyl (e.g. hydroxy and amino groups); aryl or optionally substituted aryl (e.g. hydroxy and amino groups). Preferred compounds of Formula IIIa are dicyclohexylcarbodiimide and 1-(3-Dimethylaminopropyl)-3-ethylcarbodiimide hydrochloride.

Formula IIIb:

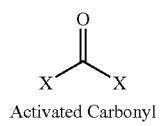

Activated Carbonyl wherein X is imidazole, tetrazole, and/or halogen. Preferred compounds of Formula IIIb are carbonyldiimidazole and carbonylditriazole.

Formula IIIc:

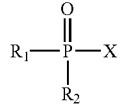

Activated Phosphorus wherein $R_1$ and $R_2$ are $C_1$-$C_8$ alkyl or cycloalkyl, $C_1$-$C_8$ optionally substituted alkyl, alkoxy or cycloalkyl (e.g. hydroxy and amino groups); aryl, alkoxy or optionally substituted aryl or alkoxy (e.g. hydroxy and amino groups) and/or halogen; and X is halogen. Preferred compounds of Formula IIIc are diphenylphosphorochloridate, phenyl phosphorodichloridate, phenylphosphonic dichloride and diphenylphosphinic chloride.

The mono- and diphosphorylating agents are shown below in the general formulas IVa-b.

Formula IVa:

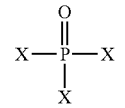

Monophosphorylating Agents wherein X is halogen. Preferred compound of Formula IVa is phosphorus oxychloride.

Formula IVb:

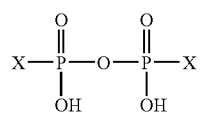

Diphosphorylating Agents wherein X is oxygen, hydroxy, or halogen, and salts thereof. Preferred compounds of Formula IVb are pyrophosphoryl chloride and pyrophosphate.

Those having skill in the art will recognize that the present invention is not limited to the following examples and that the steps in the following examples may be varied.

EXAMPLES

Example 1

Method for the Production of Diuridine Tetraphosphate, Tetrasodium Salt Using Uridine 5'-Diphosphate Uridine 5'-diphosphate disodium salt (Yamasa, Choshi, Japan; 600 grams) was dissolved in deionized water (5.4 L). The solution was passed through a Dowex 50W×4H$^+$ (Dow Chemical) column. The fractions containing uridine 5'-diphosphate were pooled and neutralized with tributylamine (Aldrich, St. Louis; 300 mL). The neutralized fractions were concentrated to an oil by using a rotary evaporator at a bath temperature of 55-60° C. The oil was dissolved in dry dimethylformamide (Aldrich, 3 L) and then dried by concentrating to an oil using a rotary evaporator (55-60° C. bath temperature). This step was repeated twice. The oil was again dissolved in dimethylformamide (3 L) and 1,1-carbonyldiimidazole (Aldrich; 100 g) was added. The solution was heated at 50° C. for 2½ hours. An additional amount of activating agent (33 grams) was added and heating continued for a further 2½ hours. The solution was again concentrated to an oil on a rotary evaporator (bath temperature at 55-60° C.). The resulting oil was dissolved in deionized water to a conductivity equal to that of 0.2 M $NH_4HCO_3$. The solution was then loaded into a column of Sephadex DEAE-A25 (Pharmacia, Upsala, Sweden; pre-swollen in 1.0 M $NaHCO_3$ and washed with 2 column volumes of deionized $H_2O$). The column was eluted with the following solutions in the following order: 60 L of 0.25 M $NH_4HCO_3$, 120 L of 0.275M $NH_4HCO_3$, 40 L of 030 M $NH_4HCO_3$ and 40 L of 0.35 M $NH_4HCO_3$. The fractions having sufficient amounts of pure diuridine tetraphosphate were pooled as determined by HPLC analysis and concentrated on a rotary evaporator (bath temperature at 55-60° C.). The resulting residue was dissolved in deionized water (1.5 L) and concentrated on a rotary evaporator. This step was repeated 15 times or until excess of bicarbonate buffer was removed. The resulting oil was dissolved in a sufficient amount of deionized water to form a ca. 10% solution, the solution charged to a Dowex 50W×4 $Na^+$ (Dow) column and eluted with deionized water. The fractions containing $U_2P_4$ were pooled and concentrated to a ca. 10-15% solution, which was lyophilized to yield $U_2P_4$ tetrasodium salt as a white solid (150 g approximately 25% yield based on uridine 5'-diphosphate).

Structure Elucidation of $P^1,P^4$-di(uridine 5'-)tetraphosphate, Tetrasodium Salt Due to the lack of adequate spectroscopic data of nonadenylated dinucleotides in the literature, a full structure elucidation of $P^1,P^4$-di(uridine 5'-)tetraphosphate, tetrasodium salt was performed by employing modern analytical techniques. The molecular weight was determined by mass spectrometry to be 878 [m/z 855, $(M-Na^+)^-$], confirming the molecular formula $C_{18}H_{22}N_4O_{23}P_4 \cdot 4Na$. The exact mass measured for $C_{18}H_{22}N_4O_{23}P_4 \cdot 3Na$ $[(M-Na^+)^-$: calculated 854.9318] was 854.9268. The measured mass differed from the theoretical mass by 5.0 milimass units (5.9 ppm) for a confidence level of 99.7%. Karl Fisher moisture analysis gave a value of 1.73% $H_2O$ and further confirmation of the molecular formula was obtained from elemental analysis: calculated for Na=10.70, found 10.81%; C:P ratio calculated 1.74, found 1.80, based on the molecular formula: $C_{18}H_{22}N_4O_{23}P_4 \cdot 4.2Na \cdot 1.1H_2O$ (FW=902.4 g/mol). The infrared spectrum showed a broad signal at 3422 $cm^{-1}$ and a signal at 1702 $cm^{-1}$, indicating the presence of hydroxyl (O—H stretch) and carbonyl (C=O stretch) functional groups. In addition, a phosphate P=O stretch was observed at 1265 $cm^{-1}$. The UV spectrum in water displayed a $\lambda_{max}$ of 262 nm with a molar absorptivity of 17,004. The specific rotation at 25° C. (c=1, $H_2O$) was determined by polarimetry to be −9.56°.

The NMR spectra are: $^1H$ NMR ($D_2O$, TMS) δ 4.11 (m, 2H), 4.14 (m, 1H), 4.25 (m, 1H), 4.27 (m, 1H), 5.84 (d, J=8.1 Hz, 1H), 5.86 (d, J=5.4 Hz, 1H), 7.81 (d, J=8.1 Hz); $^{13}C$ NMR ($D_2O$, TMS) δ 65.1 (d, J=5.5 Hz), 69.7, 73.5, 83.4 (d, J=9.4 Hz), 88.1, 102.8, 141.5, 152.9, 167.5; $^{31}P$ NMR ($D_2O$, $H_3PO_4$ std) δ −22.32 (m), −10.75 (m). The $^1H$ coupled $^{31}P$ spectrum showed a broadening of the multiplet at δ −10.75 ppm due to the introduction of $^1H$ coupling. This multiplet was therefore confirmed as $P_\alpha$. There was no effect of $^1H$ coupling on the multiplet at −22.23 ppm, assigning this by default as $P_\beta$. A Nuclear Overhauser Effect (NOE) was observed for $H_6$ to the $H_{2'}$ and $H_{3'}$ sugar protons. Because it is not possible for $H_5$ to show an NOE to the sugar protons, $H_6$ is confirmed. Additionally, $N_1$ substitution is confirmed, because no pyrimidine-sugar NOE is possible for an $N_3$ substituted structure.

Additional 2-dimensional NMR experiments were conducted to verify connectivity. HMQC shows connectivity for $H_5$ to $C_5$ and $H_6$ to $C_6$, confirming $C_5$ and $C_6$. COSY and NOE connectivity were observed for $H_5$ to $H_6$, verifying $H_5$. HMBC 3-bond connectivity was observed for: $H_6$ to $C_{1'}$, $C_6$ to $H_{1'}$, $H_{1'}$ to $C_2$, $H_6$ to $C_2$. These data thus confirm $H_{1'}$, $C_2$ and $N_1$ substitution. COSY connectivity of $H_{1'}$ to $H_{2'}$ confirms $H_{2'}$ and HMQC connectivity of $H_{1'}$ to $C_{1'}$ and $H_{2'}$ to $C_{2'}$ confirms $C_{1'}$ and $C_{2'}$. Additionally, HMBC shows 2-bond J connectivity from $H_5$ to $C_4$, confirming $C_4$. A $^{13}C$ DEPT spectrum with mult=1.5 shows the carbon at δ 65.1 inverted relative to all other carbons. This observation confirms that $C_{5'}$ is a methylene. The coupling of $^{31}P$ to carbons at δ 65.1 and 83.4 confirms $C_{5'}$ and $C_{4'}$, because $C_{4'}$ is the only coupled methyne. In addition, HMQC shows connectivity for $C_{5'}$ to $H_{5'}$ and $C_{4'}$ to $H_{4'}$, confirming $H_{4'}$ and $H_{5''}$. An NOE was observed for $H_{1'}$ to $H_{4'}$, $H_6$ to $H_{2'}$ and $H_6$ to $H_{3'}$, confirming the β anomer sugar configuration.

In conclusion, $P^1,P^4$-di(uridine 5'-)tetraphosphate, tetrasodium salt was synthesized on a 150 g scale in 25% yield from commercially available starting materials with a total reaction time of 5 hours. The crude product was efficiently purified by ion exchange chromatography and the structure of the reaction product was unambiguously proven using mass spectroscopic, NMR and other analytical techniques.

Example 2

Method for the Production of Diuridine Tetraphosphate Tetrammonium Salt Using Uridine 5'-Monophosphate Uridine 5'-monophosphate (Sigma, Milwaukee, 3.0 g, 9.26 mmol) was dissolved in dry DMF (10 mL) and tributylamine (Aldrich, 2 mL). The solution was evaporated in vacuo at 40° C. to an oil. The residue was dissolved in dry DMF (Aldrich, 8 mL) to form a solution. Carbonyldiimidazole (Aldrich, 1.65 g, 10.18 mmol) was added to this solution. The reaction was heated at 50° C. for one hour. Uridine 5'-triphosphate (Yamasa, 5.60 g, 10.18 mmol) prepared as the anhydrous tributylammonium salt in DMF (5 mL) and tributylamine (2 mL), as described in Example 3 below, was added to the reaction solution. The mixture was allowed to stir at 50° C. for three days when the solution was evaporated in vacuo to an oil, redissolved in water (5 mL) and purified by column (300×50 mm) chromatography (Sephadex DEAE-A25, 40-120µ, Aldrich, pre-swollen in 1.0 M $NaHCO_3$ and washed with 2 column volumes of deionized $H_2O$ ($H_2O \rightarrow 0.3$ M $NH_4HCO_3$ gradient). The pure fractions were concentrated in vacuo at 35° C., and $H_2O$ added and reevaporated 5 times to obtain diuridine tetraphosphate tetrammonium salt as a white solid (2.37 g, 30% yield): 92.11% pure by HPLC with the same retention time as the standard. In addition, the tetrammonium salt was analyzed by FABMS to give a mass of

[$C_{18}H_{25}N_4O_{23}P_4$ (M-H$^+$)$^-$: calculated 788.9860] 788.9857, confirming a parent formula of $C_{18}H_{26}N_4O_{23}P_4$ for the free acid].

Example 3A

Method for the Production of Diuridine Tetraphosphate Using Uridine 5'-Triphosphate (UTP)

A solution of uridine 5'-triphosphate (UTP) trisodium salt (ProBioSint, Varese, Italy; 5.86 g, 0.01 mol) in water (5 mL) was passed through a column of BioRad AG-MP 50 (Aldrich) strong cation exchange resin in its tributylamine form (50 mL bed volume) and eluted with distilled water (about 300 mL). To this solution was added tributylamine (Aldrich; 5 mL), and the suspension shaken until the pH of the aqueous fraction had risen to 8. The layers were separated and the aqueous solution evaporated to small volume, then lyophilized overnight. The residue was dissolved in dry dimethylformamide (Aldrich; 20 mL) and the solvent evaporated at 0.1 mmHg. The dried tributylamine salt was made up to 100 mL with anhydrous acetone to yield a stock solution (0.1 M in UTP). Dicyclohexylcarbodiimide (DCC) (Baker, Phillipsburg; 0.227 g, 1.2 mmol) was added to an aliquot of the foregoing UTP solution (10 mL, 1.0 mmol) and the solution stirred at room temperature for 30 minutes. The mixture was added to the triethylamine salt of uridine 5'-monophosphate (2.0 mmol, prepared by addition of triethylamine (0.5 mL) to a solution of uridine 5'-monophosphate (UMP) (Sigma; 0.648 g in DMF), and evaporating to dryness). This suspension was then evaporated to dryness, the residue made up to 5.0 mL in dry DMF, and set aside at 40° C. for 24 hours. The reaction mixture was separated by semipreparative ion-exchange chromatography (Hamilton PRP X-100 column), eluting with a gradient of 0-1.0 M ammonium bicarbonate, 5 mL/min, 30 minutes. The dinucleotide tetraphosphate eluted between 21 and 23 minutes; the product (76.7% yield based on UTP) was quantitated by comparison of its ultraviolet absorption at $\lambda_{max}$ 263 nm with that of a standard solution of $P^1,P^4$-di(uridine 5'-)tetraphosphate.

Example 3B

Method for the Production of Diuridine Tetraphosphate Using Uridine 5'-Triphosphate (UTP) and an Excess of Activating Agent Conversion of UTP to $P^1,P^4$-di(uridine 5'-)tetraphosphate can be enhanced by activation of the tributylamine salt (0.1 mmol) with a large excess of DCC (0.1 g, 0.5 mmol); in this case the deposited dicyclohexylurea was removed by filtration, the reaction mixture extracted with ether (10 mL) and the residue dissolved in dry DMF prior to treatment with tributylamine UMP (0.2 mmol). Upon chromatographic separation of the reaction mixture and quantitation by ultraviolet absorption as in Example 3A above, the uridine tetraphosphate product constituted 50.7% of the uridylate species in the mixture, corresponding to a conversion from UTP of 95.9%.

Example 4A

Method for the Production of Diuridine Tetraphosphate Using Uridine 5'-Monophosphate Activated with Carbonyldiimidazole Uridine 5'-monophosphate (UMP) (0.324 g, 1.0 mmol) was dissolved in a mixture of dry DMF (5 mL) and tributylamine (237 µL, 1 mmol) the solution was evaporated to dryness, then twice more with DMF to yield the anhydrous tributylamine salt. The residue was dissolved in DMF (5 mL) and carbonyldiimidazole (CDI) (0.81 g, 5 mmol) added. The solution was set aside for 3 hours, then methanol 324 µL, 8 mmol) added to destroy the excess of CDI. The solution was set aside for one hour. Tributylamine pyrophosphate (Sigma, 0.228 g, 0.5 mmol) was added and the suspension stirred under nitrogen at room temperature. After 3 hours the reaction was quenched with water and the mixture subjected to HPLC as in Example 3A above. Yield of $P^1,P^4$-di(uridine 5'-)tetraphosphate as quantitated by its absorbance at 263 nm was 9.3%.

Example 4B

Method for the Production of Diuridine Tetraphosphate Using Uridine 5'-Monophosphate Activated with Diphenyl Phosphochloridate The anhydrous tributylamine salt of UMP (1.0 mmol), prepared essentially as above, was dissolved in a mixture of dry dioxane (5 mL) and DMF (1 mL). Diphenyl phosphochloridate (0.3 mL) and tributylamine (0.3 mL) were added and the solution set aside at room temperature for 3 hours. The solvent was evaporated and the residue shaken with ether (~10 mL), then set aside at 4° C. for 30 minutes. The ether was decanted and the residue was dissolved in a solution of tributylamine pyrophosphate (0.228 g, 0.5 mmol) in DMF (3 mL). The solution was stored under nitrogen at room temperature. After 3 hours the reaction was quenched with water and the mixture subjected to HPLC as in Example 3A above. Yield of $P^1,P^4$-di(uridine 5'-)tetraphosphate as quantified by its absorbance at 263 nm was 9.6%.

Example 5

Method for the Production of Diuridine Tetraphosphate Using Uridine, Phosphorus Oxychloride and Pyrophosphate Uridine (Aldrich, 0.244 g, 1 mmol) was dissolved in trimethyl phosphate (Aldrich, 5 mL) and tributylamine (466 uL, 2 mmol) added. The solution was stirred at 0 degrees during the addition of phosphorus oxychloride (0.153 g (93.2 uL), 1 mmol), and the resulting suspension stirred at 0° C. for 3 hours. Tributylamine pyrophosphate (0.228 g) was added and the suspension stirred at room temperature for 3 hours. The reaction was quenched with 1.0 M aqueous triethylamine bicarbonate and the mixture extracted with methylene chloride to remove trimethyl phosphate. The aqueous solution was subjected to HPLC as in Example 3A above. Conversion of uridine to $P^1,P^4$-di(uridine 5'-)tetraphosphate as quantitated by absorbance of the latter at 263 nm was 6.83%.

Example 6

Method for the Production of Diuridine Tetraphosphate Using Uridine 5'-Monophosphate and Pyrophosphoryl Chloride Uridine 5'-monophosphate (UMP) (64.8 mg, 0.2 mmol) was dissolved in dry pyridine (1 mL) and stirred in ice during the addition of pyrophosphoryl chloride (13.9 uL (25 mg), 0.1 mmol). The solution became cloudy almost immediately, then a copious semicrystalline white precipitate formed which became a gummy mass within 1-2 minutes. The mixture was stored at room temperature overnight, the quenched with water and subjected to HPLC as in Example 3A above. Yield of $P^1,P^4$-di(uridine 5'-)tetraphosphate as quantitated by its absorbance at 263 nm was 15.8%. A substantial amount of $P^1, P^3$-di(uridine 5'-)triphosphate (25.4%) was obtained as the major by-product.

Example 7

Aqueous Stability and Solubility of $P^1,P^4$-di(uridine 5'-)tetraphosphate, Tetrasodium Salt The solubility of $P^1,P^4$-di(uridine 5'-)tetraphosphate, tetrasodium salt in water was determined by adding portions of solid to a known volume of deionized water until the solution became turbid. The maximum solubility in water was thus determined to be ca. 900 mg/mL. Stability studies of the solid or aqueous solutions incubated at low (5° C.) and elevated temperatures (40° C.) showed that less than 1.5% degradation occurs over a three month period as determined by HPLC analysis. The tetrasodium salt of $P^1,P^4$-di(uridine 5'-) tetraphosphate was thus determined to have an excellent solubility and stability profile suitable for pharmaceutical applications.

Example 8

Toxicity of $P^1,P^4$-di(uridine 5'-)tetraphosphate, Tetrasodium Salt in Animals The nonclinical toxicologic profile of $P^1,P^4$-di(uridine 5'-)tetraphosphate, tetrasodium salt has been evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examined local ocular tolerance and subchronic ocular toxicity after multiple daily administrations over a six-week period. In addition, $P^1,P^4$-di(uridine 5'-)tetraphosphate, tetrasodium salt has also been tested in two single-dose acute inhalation toxicity studies in rat and dog, and one single-dose acute intravenous toxicity study in dogs.

The results of these studies show that $P^1,P^4$-di(uridine 5'-)tetraphosphate, tetrasodium salt is nongenotoxic in a battery of genetic toxicology assays. No adverse findings were seen in the ocular toxicology studies. A low degree of acute toxicity was seen in single dose inhalation (rats, dogs) and intravenous (dogs) toxicity studies. $P^1,P^4$-di(uridine 5'-)tetraphosphate, tetrasodium salt was therefore determined to have an excellent toxicology profile with a wide safety margin for dosing in humans.

Example 9

Safety and Efficacy of $P^1,P^4$-di(uridine 5'-)tetraphosphate, Tetrasodium Salt in Normal Human Volunteers $P^1,P^4$-di(uridine 5'-)tetraphosphate, tetrasodium salt was evaluated in a Phase I, double-blind, placebo-controlled, escalating dose, safety and tolerability study in 75 normal healthy male volunteers. Forty non-smokers and 35 smokers were evaluated in 5 dosing cohorts of 16 volunteers, comprised of 12 receiving a single aerosolized dose of $P^1,P^4$-di(uridine 5'-)tetraphosphate, tetrasodium salt (20-400 mg) and 4 receiving placebo (normal saline). No serious adverse events were reported. There were no significant changes in $FEV_1$, FVC, MMEF, clinical laboratory, 12-lead ECG, or urinalysis results in either the placebo or active drug groups. In smokers, $P^1,P^4$-di(uridine 5'-)tetraphosphate, tetrasodium salt produced a 2-fold to 7-fold dose-dependent increase in the weight of sputum expectorated within 5 minutes of dosing, and stimulation of sputum expectoration was sustained over the next hour of sputum collection. The effect of $P^1,P^4$-di(uridine 5'-) tetraphosphate, tetrasodium salt to induce the expectoration of sputum in non-smokers was also observed. In conclusion, $P^1,P^4$-di(uridine 5'-)tetraphosphate, tetrasodium salt is safe and well-tolerated in normal male subjects and is effective in stimulating the expectoration of sputum when compared to placebo.

Example 10

Method for the Production of Diuridine Tetraphosphate, Potassium Salt Using Uridine 5'-Diphosphate Uridine 5'-diphosphate disodium salt is dissolved in deionized water. The solution is passed through a Dowex 50W× 4H+ (Dow Chemical) column. The fractions containing uridine 5'-diphosphate are pooled and neutralized with tributylamine (Aldrich, St. Louis, Mo.). The neutralized fractions are concentrated to an oil form by using a rotary evaporator at a bath temperature of 55-60° C. The oil is dissolved in dry dimethylformamide (Aldrich) and then dried by concentrating to an oil using a rotary evaporator (55-60° C. bath temperature). This step is repeated. The oil is dissolved in dimethylformamide and 1,1-carbonyldiimidazole (Aldrich) is added. The solution is heated at 50° C. An additional amount of activating agent is added and heating continued. The solution is again concentrated to an oil form on a rotary evaporator (bath temperature at 55-60° C.). The resulting oil is dissolved in deionized water. The solution is then loaded into a column of Sephadex DEAE-A25 (Pharmacia, Upsala, Sweden; pre-swollen in 1.0 M $NaHCO_3$ and washed with 2 column volumes of deionized $H_2O$). The column is eluted with the following solutions in the following order: 60 L of 0.25 M $NH_4HCO_3$, 120 L of 0.275M $NH_4HCO_3$, 40 L of 030 M $NH_4HCO_3$ and 40 L of 0.35 M $NH_4HCO_3$. The fractions having sufficient amounts of pure diuridine tetraphosphate were pooled as determined by HPLC analysis and concentrated on a rotary evaporator (bath temperature at 55-60° C.). The resulting residue is dissolved in deionized water (1.5 L) and concentrated on a rotary evaporator. This step is repeated until excess of the bicarbonate buffer is removed. The resulting oil is dissolved in a sufficient amount of deionized water to form a ca. 10% solution, the solution charged to a Dowex 50W×4H⁺ (Dow) column, which is prewashed with potassium bicarbonate, and eluted with deionized water. The fractions containing $U_2P_4$ are pooled and concentrated, then lyophilized to yield $U_2P_4$ tetrapotassium salt as a solid.

Example 11

Method for the Production of Diuridine Tetraphosphate, Lithium Salt Using Uridine 5'-Diphosphate Uridine 5'-diphosphate disodiuim salt is dissolved in deionized water. The solution is passed through a Dowex 50W×4H+ (Dow Chemical) column. The fractions containing uridine 5'-diphosphate are pooled and neutralized with tributylamine (Aldrich, St. Louis, Mo.). The neutralized fractions are concentrated to an oil form by using a rotary evaporator at a bath temperature of 55-60° C. The oil is dissolved in dry dimethylformamide (Aldrich) and then dried by concentrating to an oil form using a rotary evaporator (55-60° C. bath temperature). This step is repeated. The oil is dissolved in dimethylformamide and 1,1-carbonyldiimidazole (Aldrich) is added. The solution is heated at 50° C. An additional amount of activating agent is added and heating continued. The solution is again concentrated to an oil on a rotary evaporator (bath temperature at 55-60° C.). The resulting oil is dissolved in deionized water. The solution is then loaded into a column of Sephadex DEAE-A25 (Pharmacia, Upsala, Sweden; pre-swollen in 1.0 M $NaHCO_3$ and washed with 2 column volumes of deionized $H_2O$). The column is eluted with the following solutions in the following order: 60 L of 0.25 M $NH_4HCO_3$, 120 L of 0.275M $NH_4HCO_3$, 40 L of 030 M $NH_4HCO_3$ and 40 L of 0.35 M $NH_4HCO_3$. The fractions having sufficient amounts of pure diuridine tetraphosphate were pooled as determined by HPLC analysis and concentrated on a rotary evaporator (bath temperature at 55-60° C.). The resulting residue is dissolved in deionized water (1.5 L) and concentrated on a rotary evaporator. This step is repeated until excess of the bicarbonate buffer is removed. The resulting oil is dissolved in a sufficient amount of deionized water to form a ca. 10% solution, the solution charged to a Dowex 50W×4H⁺ (Dow) column, which is prewashed with lithium carbonate, and eluted with deionized water. The fractions containing $U_2P_4$ are pooled and concentrated, then lyophilized to yield $U_2P_4$ tetralithium salt as a solid.

Example 12

Solubility and Stability of $P^1,P^4$-di(uridine 5'-)tetraphosphate, Tetralithium Salt The solubility of $P^1,P^4$-di(uridine 5'-)tetraphosphate, tetralithium salt in water is determined by adding portions of solid to a known volume of deionized water until the solution becomes turbid. Stability studies are performed by incubating the solid or aqueous solutions at low (5° C.) and elevated temperatures (40° C.) for a period of time. The tetralithium salt of $P^1,P^4$-di(uridine 5'-)tetraphosphate is determined to have an excellent solubility and stability profile suitable for pharmaceutical applications.

Example 13

Solubility and Stability of $P^1,P^4$-di(uridine 5'-)tetraphosphate, Tetrapotassium Salt The solubility of $P^1,P^4$-di(uridine 5'-)tetraphosphate, tetrapotassium salt in water is determined by adding portions of solid to a known volume of deionized water until the solution became turbid. Stability studies are performed by incubating the solid or aqueous solutions at low (5° C.) and elevated temperatures (40° C.) for a period of time. The tetrapotassium salt of $P^1,P^4$-di(uridine 5'-)tetraphosphate is determined to have an excellent solubility and stability profile suitable for pharmaceutical applications.

Example 14

Toxicity of $P^1,P^4$-di(uridine 5'-)tetraphosphate, Tetralithium Salt in Animals The nonclinical toxicologic profile of $P^1,P^4$-di(uridine 5'-)tetraphosphate, tetralithium salt is evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examines local ocular tolerance and subchronic ocular toxicity after multiple daily administrations over a six-week period. No adverse findings are seen in the ocular toxicology studies. The $P^1,P^4$-di(uridine 5'-)tetraphosphate, tetralithium salt has an excellent toxicology profile with a wide safety margin.

Example 15

Toxicity of $P^1,P^4$-di(uridine 5'-)tetraphosphate, Tetrapotassium Salt in Animals The nonclinical toxicologic profile of $P^1,P^4$-di(uridine 5'-)tetraphosphate, tetrapotassium salt is evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examines local ocular tolerance and subchronic ocular toxicity after multiple daily administrations over a six-week period. No adverse findings are seen in the ocular toxicology studies. The $P^1,P^4$-di(uridine 5'-)tetraphosphate, tetrapotassium salt has an excellent toxicology profile with a wide safety margin.

Example 16

Method for the Production of Diuridine Tetraphosphate, Tetraammonium Salt Using Uridine 5'-Diphosphate The solution of tetraammonium salt of $U_2P_4$ in the ammonium-bicarbonate buffer was prepared and concentrated on a rotary evaporator to remove the excess of bicarbonate buffer according to Example 1.

The resulting oil is dissolved in a sufficient amount of deionized water to form a ca. 10% solution, the solution is frozen and lyophilized to give $P^1,P^4$-di(uridine 5'-) tetraphosphate, tetraamonium salt as a gummy powder in approximately 25% yield. The $^1$H, $^{31}$P and $^{13}$C NMR data are in accord with that of the structure of $U_2P_4$.

Example 17

Method for the Large Scale Production of Diuridine Tetraphosphate, Disodiumdipotassium Salt from Diuridine Tetraphosphate, Tetraammonium Salt Approximately one kilogram of $P^1,P^4$-di(uridine 5'-)tetraphosphate, tetraammonium salt is dissolved in a sufficient amount of deionized water to form a ca. 10% solution. The amount of $U_2P_4$ present in the solution is quantitated by comparison of the ultraviolet absorption at $\lambda_{max}$ 263 nm of an accurately diluted sample with that of a standard solution of $P^1,P^4$-di(uridine 5'-)tetraphosphate at 0.1 mg/mL. This solution of $P^1,P^4$-di(uridine 5'-) tetraphosphate, tetraammonium salt of known concentration is then cooled to 0° C. and treated with an ice cold solution containing two equivalents of sodium acetate and two equivalents of potassium bicarbonate in deionized water over two hours. The resulting solution is placed on a large rotary evaporator in portions and is concentrated under vacuum at below 60° C. to give a thick liquid, which is dissolved in deionized water to give a ca. 10% solution. The evaporation and dilution processes are repeated two more times to remove volatile ammonium salts and then the residue is dissolved in water to form a ca. 10% solution which is lyophilized to yield $U_2P_4$, disodiumdipotassium salt as a white solid in excellent yield and purity.

Example 18

Aqueous Stability and Solubility of $P^1,P^4$-di(uridine 5'-)tetraphosphate, Disodiumdipotassium Salt The solubility of $P^1,P^4$-di(uridine 5'-)tetraphosphate, disodiumdipotassium salt in water is determined by adding portions of solid to a known volume of deionized water until the solution becomes turbid. Stability studies are performed by incubating the solid or aqueous solutions at low (5° C.) and elevated temperatures (40° C.) for a period of time. The disodiumdipotassium salt of $P^1,P^4$-di(uridine 5'-)tetraphosphate is determined to have an excellent solubility and stability profile suitable for pharmaceutical applications.

Example 19

Toxicity of $P^1,P^4$-di(uridine 5'-)tetraphosphate, Disodiumdipotassium Salt in Animals The nonclinical toxicologic profile of $P^1,P^4$-di(uridine 5'-)tetraphosphate, disodiumdipotassium salt is evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examines local ocular tolerance and subchronic ocular toxicity after multiple daily administrations over a six-week period. No adverse findings are seen in the ocular toxicology studies. The $P^1,P^4$-di(uridine 5'-)tetraphosphate, disodiumdipotassium salt has an excellent toxicology profile with a wide safety margin.

Example 20

Method for the Production of Diuridine Tetraphosphate, Monopotassiumtrilithium Salt Using Uridine 5'-Diphosphate Uridine 5'-diphosphate disodium salt is dissolved in deionized water. The solution is passed through a Dowex 50W× 4H$^+$ (Dow Chemical) column. The fractions containing uridine 5'-diphosphate are pooled and neutralized with tributylamine (Aldrich, St. Louis, Mo.). The neutralized fractions are concentrated to an oil form by using a rotary evaporator at a bath temperature of 55-60° C. The oil is dissolved in dry dimethylformamide (Aldrich) and then dried by concentrating to an oil using a rotary evaporator (55-60° C. bath temperature). This step is repeated. The oil is dissolved in dimethylformamide and 1,1-carbonyldiimidazole (Aldrich) is added. The solution is heated at 50° C. An additional amount of activating agent is added and heating continued. The solution is again concentrated to an oil form on a rotary evaporator (bath temperature at 55-60° C.). The resulting oil is dissolved in deionized water. The solution is then loaded into a column of Sephadex DEAE-A25 (Pharmacia, Upsala, Sweden; pre-swollen in 1.0 M NaHCO$_3$ and washed with 2 column volumes of deionized H$_2$O). The column is eluted with the following solutions in the following order: 60 L of 0.25 M NH$_4$HCO$_3$, 120 L of 0.275M NH$_4$HCO$_3$, 40 L of 030 M NH$_4$HCO$_3$ and 40 L of 0.35 M NH$_4$HCO$_3$. The fractions having sufficient amounts of pure diuridine tetraphosphate are pooled as determined by HPLC analysis and concentrated on a rotary evaporator (bath temperature at 55-60° C.). The resulting residue is dissolved in deionized water (1.5 L) and concentrated on a rotary evaporator. This step is repeated until the excess of bicarbonate buffer is removed. The resulting oil is dissolved in a sufficient amount of deionized water to form a ca. 10% solution, and the amount of $U_2P_4$ present in the solution is quantitated by comparison of its ultraviolet absorption at $\lambda_{max}$ 263 nm with that of a standard solution of $P^1,P^4$-di(uridine 5'-)tetraphosphate as in Example 7. This solution of $P^1,P^4$-di(uridine 5'-)tetraphosphate, tetraammonium salt of known concentration is then cooled to 0° C. and treated with an ice cold solution containing three equivalents of lithium acetate and one equivalent of potassium bicarbonate. The resulting solution is placed on a rotary evaporator and is concentrated under vacuum at below 60° C. to give a thick liquid, which is dissolved in deionized water. The evaporation and dilution processes are repeated two more times to remove volatile ammonium salts and then the residue is dissolved in water to form a ca. 10% solution which is lyophilized to yield $U_2P_4$, monopotassiumtrilithium salt as a white solid.

Example 21

Method for the Production of Diuridine Tetraphosphate, Monolithiummonopotassiumdisodium Salt Using Uridine 5'-Diphosphate Uridine 5'-diphosphate disodiuim salt is dissolved in deionized water. The solution is passed through a Dowex 50W×4H$^+$ (Dow Chemical) column. The fractions containing uridine 5'-diphosphate are pooled and neutralized with tributylamine (Aldrich, St. Louis, Mo.). The neutralized fractions are concentrated to an oil form by using a rotary evaporator at a bath temperature of 55-60° C. The oil is dissolved in dry dimethylformamide (Aldrich) and then dried by concentrating to an oil form using a rotary evaporator (55-60° C. bath temperature). This step is repeated. The oil is dissolved in dimethylformamide and 1,1-carbonyldiimidazole (Aldrich) is added. The solution is heated at 50° C. An additional amount of activating agent is added and heating continued. The solution is again concentrated to an oil on a rotary evaporator (bath temperature at 55-60° C.). The resulting oil is dissolved in deionized water. The solution is then loaded into a column of Sephadex DEAE-A25 (Pharmacia, Upsala, Sweden; pre-swollen in 1.0 M $NaHCO_3$ and washed with 2 column volumes of deionized $H_2O$). The column is eluted with the following solutions in the following order: 60 L of 0.25 M $NH_4HCO_3$, 120 L of 0.275M $NH_4HCO_3$, 40 L of 030 M $NH_4HCO_3$ and 40 L of 0.35 M $NH_4HCO_3$. The fractions having sufficient amounts of pure diuridine tetraphosphate were pooled as determined by HPLC analysis and concentrated on a rotary evaporator (bath temperature at 55-60° C.). The resulting residue is dissolved in deionized water (1.5 L) and concentrated on a rotary evaporator. This step is repeated until excess of the bicarbonate buffer is removed. The resulting oil is dissolved in a sufficient amount of deionized water to form an approximately 10% solution, and the amount of $U_2P_4$ present in the solution is quantitated by comparison of its ultraviolet absorption at $\lambda_{max}$ 263 nm with that of a standard solution of $P^1,P^4$-di(uridine 5'-)tetraphosphate as in Example 7. This solution of $P^1,P^4$-di(uridine 5'-)tetraphosphate, tetraammonium salt of known concentration is then cooled to 0° C. and treated with an ice cold solution containing one equivalent of lithium formate, one equivalent of potassium bicarbonate, and two equivalents of sodium ion in the form of sodium carbonate. The resulting solution is placed on a rotary evaporator and is concentrated under vacuum at below 60° C. to give a thick liquid, which is dissolved in deionized water. The evaporation and dilution processes are repeated two more times to remove volatile ammonium salts and then the residue is dissolved in water to form an approximately 10% solution which is lyophilized to yield $U_2P_4$, monolithiummonopotassiumdisodium salt as a white solid.

Example 22

Solubility and Stability of $P^1,P^4$-di(uridine 5'-)tetraphosphate, Monolithiummonopotassiumdisodium Salt The solubility of $P^1,P^4$-di(uridine 5'-)tetraphosphate, monolithiummonopotassiumdisodium salt in water is determined by adding portions of solid to a known volume of deionized water until the solution becomes turbid. Stability studies are performed by incubating the solid or aqueous solutions at low (5° C.) and elevated temperatures (40° C.) for a period of time. The monolithiummonopotassiumdisodium salt of $P^1,P^4$-di(uridine 5'-)tetraphosphate is determined to have an excellent solubility and stability profile suitable for pharmaceutical applications.

Example 23

Solubility and Stability of $P^1,P^4$-di(uridine 5'-)tetraphosphate, Monopotassiumtrilithium Salt The solubility of $P^1,P^4$-di(uridine 5'-)tetraphosphate, monopotassiumtrilithium salt in water is determined by adding portions of solid to a known volume of deionized water until the solution became turbid. Stability studies are performed by incubating the solid or aqueous solutions at low (5° C.) and elevated temperatures (40° C.) for a period of time. The monopotassiumtrilithium salt of $P^1,P^4$-di(uridine 5'-)tetraphosphate is determined to have an excellent solubility and stability profile suitable for pharmaceutical applications.

Example 24

Toxicity of $P^1,P^4$-di(uridine 5'-)tetraphosphate, Monopotassiumtrilithium Salt in Animals The nonclinical toxicologic profile of $P^1,P^4$-di(uridine 5'-)tetraphosphate, monopotassiumtrilithium salt is evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examines local ocular tolerance and subchronic ocular toxicity after multiple daily administrations over a six-week period. No adverse findings are seen in the ocular toxicology studies. The $P^1,P^4$-di(uridine 5'-)tetraphosphate, monopotassiumtrilithium salt has an excellent toxicology profile with a wide safety margin.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of treating dry eye in a mammal by administering to the mammal a pharmaceutical formulation comprising $P^1$, $P^4$-di(uridine 5'-)tetraphosphate, tetralithium salt; or $P^1$, $P^4$-di(uridine 5'-)tetraphosphate, tetrapotassium salt; in a pharmaceutically acceptable carrier.

2. A method of treating retinal detachment in a mammal by administering to the mammal a pharmaceutical formulation comprising $P^1,P^4$-di(uridine 5'-)tetraphosphate, tetralithium salt; or $P^1,P^4$-di(uridine 5'-)tetraphosphate, tetrapotassium salt; in a pharmaceutically acceptable carrier.

3. A method of treating dry eye in a mammal by administering to the mammal an effective dry eye treatment amount of a compound of Formula I:

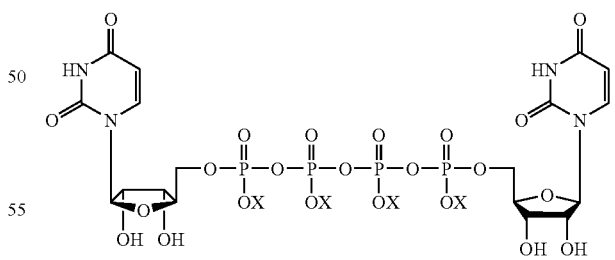

Formula I wherein:
each X is independently Li, Na, or K, provided that not all X's are Li, Na, or K.

4. The method according to claim 3, wherein said compound is $P^1,P^4$-di(uridine 5'-) tetraphosphate, tetra-alkali metal salt, in which the tetra-alkali metal cations of said salt are selected from the group consisting of: monosodium/tripotassium, disodium/dipotassium, trisodium/monopotassium, monopotassium/trilithium, dipotassium/dilithium, tripotassium/monolithium, monosodium/trilithium, disodium/dilithium, trisodium/monolithium, monosodium/monolithium/dipotassium, monosodium/dilithium/monopotassium and disodium/monolithium/monopotassium.

5. A method of treating retinal detachment in a mammal by administering an effective dry eye treatment amount of a compound of Formula I:

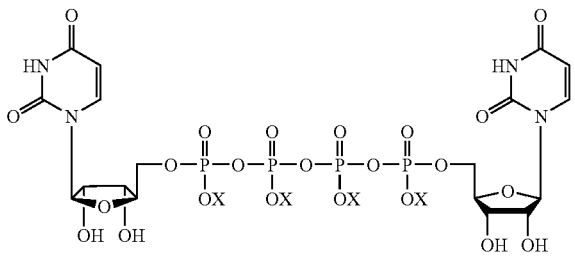

Formula I wherein:

each X is independently Li, Na, or K, provided that not all X's are Li, Na, or K.

6. The method according to claim 5, wherein said compound is $P^1,P^4$-di(uridine 5'-) tetraphosphate, tetra-alkali metal salt, in which the tetra-alkali metal cations of said salt are selected from the group consisting of: monosodium/tripotassium, disodium/dipotassium, trisodium/monopotassium, monopotassium/trilithium, dipotassium/dilithium, tripotassium/monolithium, monosodium/trilithium, disodium/dilithium, trisodium/monolithium, monosodium/monolithium/dipotassium, monosodium/dilithium/monopotassium and disodium/monolithium/monopotassium.

* * * * *